United States Patent [19]
Romer et al.

[11] Patent Number: 4,784,994
[45] Date of Patent: Nov. 15, 1988

[54] PROCESS FOR THE TREATMENT OF INFLAMMATORY AND ALLERGIC DISEASES

[75] Inventors: Axel Romer, Hurth-Gleuel; Jorg Hager, Cologne, both of Fed. Rep. of Germany

[73] Assignee: A. Nattermann & Cie GmbH, Cologne, Fed. Rep. of Germany

[21] Appl. No.: 49,727

[22] Filed: May 12, 1987

[30] Foreign Application Priority Data

Jun. 20, 1986 [DE] Fed. Rep. of Germany ....... 3620674

[51] Int. Cl.$^4$ .............................................. A61K 31/33
[52] U.S. Cl. ................................................. 514/183
[58] Field of Search ........................................ 514/183

[56] References Cited

U.S. PATENT DOCUMENTS

| 4,352,799 | 10/1982 | Renson et al. | 424/244 |
| 4,514,386 | 4/1985 | Yamahiro et al. | 424/81 |
| 4,525,347 | 6/1985 | Inagi et al. | 424/81 |
| 4,540,572 | 9/1985 | Seth | 424/81 |
| 4,543,251 | 9/1985 | Kamishita | 424/81 |
| 4,683,242 | 7/1987 | Poser | 514/539 |

OTHER PUBLICATIONS

Chem. Abst.-96, (1982)-187324f.
Chem. Abst.-104, (1986)-50881z.
R. Weber et al., Bulletin De La Soc. Chim. De France, 1976, (7/8), pp. 1124–1126.
H. Sies, Oxidative Stress, 1985, pp. 1–8.
R. C. Allen et al., Biochemical and Biophysical Research Communications, vol. 47, No. 4, pp. 679–684, (1972).
Knox Van Dyke et al., Microchemical Journal 25, 514–523, (1980).
David A. Hume et al., Biochem. J., (1981), vol. 198, pp. 661–667.
Enrique Cadenas et al., Biochem. J., (1980), vol. 192, pp. 303–309.
Alberto Boveris et al., Federation Proceedings, vol. 40, No. 2, (1981), pp. 195–198.
Robert C. Young et al., The New England Journal of Medicine, vol. 305, No. 3, (1981), pp. 139–153.
Thomas R. Tritton et al., Science, vol. 217, (1982), pp. 248–250.
Albrecht Wendel, Methods in Enzymology, vol. 77, (1981), pp. 325–333.

Primary Examiner—Stanley J. Friedman
Attorney, Agent, or Firm—Pearne, Gordon, McCoy & Granger

[57] ABSTRACT

The invention relates to a process for the treatment of inflammatory and allergic skin diseases.

2 Claims, No Drawings

PROCESS FOR THE TREATMENT OF INFLAMMATORY AND ALLERGIC DISEASES

The invention relates to a formulation for the topical application of ebselen in an ointment base, a process for its preparation, and its use in the treatment of inflammatory and allergic skin diseases, more particularly psoriasis.

Ebselen is a benzisoselenazol derivative having the designation 2-phenyl-1.2-benzisoselenazol-3(2H)-one and is known from U.S. Pat. No. 4,352,799. This patent specification also discloses the use of ebselen in the treatment of rheumatic diseases.

The invention relates to ebselen ointments for the treatment of skin conditions characterized by epidermal functional disorders, e.g. psoriasis.

Psoriasis is a chronic skin disease characterized by epidermal hyperplasia and the resulting enormously accelerated cell proliferation in the skin. Erythema as an indication of the inflammation is covered with silvery scales can be peeled off easily. The disease is a life-long disorder which can both occur at limited areas such as the scalp, elbows or knees, and cover the entire skin. In many patients the condition is tolerable and causes only minor inconvenience. In a few cases psoriasis may become a disease which threatens life. The majority of cases lie between these two extremes, with psoriasis being the cause of considerable inconvenience and social difficulties.

The treatment of psoriasis is unsatisfactory inasmuch as although the abnormal changes can be made to disappear temporarily, the patient cannot be protected from new outbreaks. The current treatment, which is not curative, is to control the increased cell growth with hormones such as corticosteroids or preparations used in cancer therapy, e.g. methotrexate. Dithranol, etretinate and methoxsalen have also been used for example. However, in some cases these compounds exhibit very unpleasant side effects, particularly on the kidney and liver. There is therefore a need for new preparations which have good activity, which should as far as possible be curative, with minor side effects.

It has now surprisingly been found that ebselen ointment can be used as an effective formulation in the treatment of inflammatory and allergic skin diseases, such as, for example, psoriasis, eczemas, e.g. chronic eczema, dermatitis, e.g. contact dermatitis and neurodermatitis, and related diseases.

Ebselen (2-phenyl-1.2-benzisoselenazol-3(2H)-one) is a known compound which can be used for the treatment of rheumatic diseases (U.S. Pat. No. 4,352,799). It is prepared by known processes (R. Weber, M. Renson, Bulletin de la Soc. Chim. de France 1976 (7/8) 1124–1126 by reacting 2-methylseleno-N-phenylbenzamide with phosphorous pentachloride followed by hydrolysis.

The invention relates to the formulation of ebselen for topical application with an active substance content of 0.1 to 10% by weight of ebselen. Formulations with an active substance content of 1 to 5% by weight of ebselen are particularly preferred. Various compositions are possible for the ointment base, e.g. mixture of hydrocarbons such as liquid paraffin, viscous paraffin oil, white vaseline with mono-, di- or triglycerides such as glycerine monostearate, caprylic-capric acid di- and triglyceride, fatty alcohols such as cetyl stearyl alcohol, possibly with the addition of polyoxyethylene fatty alcohol ethers, such as polyoxyethylene cetyl stearyl ether.

The following compositions are particularly preferred:

(a)
  10–15% by weight glycerine monostearate
  10–20% by weight caprylic-capric acid triglycerides
  20–30% by weight white vaseline
  25–35% by weight liquid paraffin (b)
  25–35% by weight viscous paraffin oil
  25–35% by weight white vaseline
  20–30% by weight cetyl stearyl alcohol (c)
  10–15% by weight white vaseline
  15–25% by weight Softisan ® 601
  5–10% by weight Miglyol ®-Gel B
  35–45% by weight Miglyol ® 829

Softisan ® 601 is the trade name for a mixture of tri-and partial glycerides of natural fatty acids with skin-compatible non-ionic emulsifiers, e.g. hydrogenated coconut oil. Miglyol ®-Gel B is the trade name for a Miglyol 812-neutral oil thickened with a modified montmorillonite. Miglyol 812-neutral oil is a caprylic/caparic acid triglyceride.

(d)
  10–15% by weight glycerine monostearate
  75–85% by weight caprylic&capric acid triglycerides
  3% by weight Ceteareth-12

Ceteareth-12 is the polyoxyethylene-cetylstearyl ether with n=12.

(e)
  10–20% by weight of white vaseline
  20–30% by weight Softisan ® 601
  10–15% by weight Miglyol ®-Gel B
  40–50% by weight Miglyol ® 829

The invention also relates to a process for the preparation of formulations for topical application. In this process ebselen is ground to a particle size less than 5 μm and is milled in batches with the melted and again cold-stirred ointment base in the active substance/ointment base weight ration of 1:1 to 1:5 in an ointment mill to form a homogeneous substance, whereupon it is homogenized with the principal part of the ointment base. The ebselen ointment prepared in this way is administered topically for the treatment of inflammatory and allergic skin diseases.

The ebselen concentration in the topical drug form is advantageously 0.1 to 10% by weight, preferably 1 to 5% by weight.

The preparation of the formulations according to the invention is explained in detail by the following examples.

EXAMPLE 1

General procedure

The acive substance, ebselen, is ground to a particle size less than 5 μm and milled in batches with the melted, mixed an cold-stirred ointment base to form a homogenous substance, using an ointment mill, until the active substance/ointment base weight ratio is 1:1 to 1:5. The remaining ointment base is then added to the homogenous active substance mix which is processed to uniformity.

The resulting suspension ointments are packed in tubes by means of conventional filling equipment.
Ebselen: 1%

Glycerine monostearate: 15%
Caprylic/capric acid triglycerides: 20%
white vaseline: 30%
liquid paraffin: 34%
Appearance: white, spreadable
pH value: 5.5
Viscosity in mPas: 90,000.

EXAMPLE 2

Procedure as in Example 1

Ebselen: 1%
Viscous paraffin oil: 35%
white vaseline: 34%
Cetyl stearyl alcohol: 30%
Appearance: white, spreadable
pH value: 6.0
Viscosity in mPas: 20,000

EXAMPLE 3

Procedure as in Example 1

Ebselen: 5%
white vaseline: 15%
Sofisan® 601: 25%
Miglyol®-Gel B: 10%
Miglyol® 829: 45%
Appearance: white, spreadable
pH value: 5.6
Viscosity in mPas: 12,000

EXAMPLE 4

Procedure as in Example 1

Ebselen: 5%
Glycerine monostearate: 15%
Caprylic/capric acid triglycerides: 77%
Ceteareth-12: 3%
Appearance: white, spreadable
pH-value: 5.8
Viscosity in mPas: 20,000

EXAMPLE 5

Procedure as in Example 1

Ebselen: 1%
Glycerine monostearate: 15.7%
Caprylic/capric acid triglyceride: 80.3%
Ceteareth-12: 3%
Appearance: white, spreadable
pH-value: 5.6
Viscosity in mPas: 12,000

EXAMPLE 6

Procedure as in Example 1

Ebselen: 1%
white vaseline: 16%
Softisan® 601: 26%
Miglyol®-Gel B: 11%
Miglyol® 829: 46%
Appearance: white, spreadable
pH value: 5.6
Viscosity in mPas: 41,000

What we claim is:

1. A process for the treatment of skin allergic diseases in human beings comprising applying topically to the affected skin of the human being to be treated, an ointment formulation comprising 0.1 to 10% by weight of 2-phenyl-1.2-benzisoselenazol-3(2H)-one in the final ointment.

2. A process for the treatment of psoriasis in human beings comprising applying topically to the affected skin of the human being to be treated, an ointment formulation comprising 0.1 to 10% by weight of 2-phenyl-1.2-benzisoselenazol-3(2H)-one in the final ointment.

* * * * *